(12) United States Patent
Preissman

(10) Patent No.: US 7,510,579 B2
(45) Date of Patent: Mar. 31, 2009

(54) ENHANCED VISIBILITY MATERIALS FOR IMPLANTATION IN HARD TISSUE

(75) Inventor: Howard Preissman, Stuart, FL (US)

(73) Assignee: ArthroCare Corporation, Austin, TX (US)

( * ) Notice: Subject to any disclaimer, the term of this patent is extended or adjusted under 35 U.S.C. 154(b) by 445 days.

(21) Appl. No.: 09/828,539

(22) Filed: Apr. 5, 2001

(65) Prior Publication Data

US 2001/0012968 A1    Aug. 9, 2001

Related U.S. Application Data

(60) Continuation of application No. 09/420,093, filed on Oct. 18, 1999, now Pat. No. 6,231,615, which is a division of application No. 08/950,256, filed on Oct. 14, 1997, now Pat. No. 6,309,420.

(51) Int. Cl.
*A61F 2/02* (2006.01)
*A61F 2/04* (2006.01)

(52) U.S. Cl. .................. 623/23.72; 623/20.61

(58) Field of Classification Search ............. 623/23.73, 623/17.12, 923, 902, 917, 919, 908, 23.61–23.63, 623/23.51, 23.56, 23.58, 23.72; 600/431; 606/76, 77, 92, 94, 97; 523/117
See application file for complete search history.

(56) References Cited

U.S. PATENT DOCUMENTS

| | | |
|---|---|---|
| 3,701,771 A | 10/1972 | Almen et al. |
| 3,882,858 A | 5/1975 | Klemm |
| 3,919,773 A | 11/1975 | Freeman |
| 4,288,355 A | 9/1981 | Anderson et al. |
| 4,341,691 A | 7/1982 | Anuta |
| 4,364,921 A | 12/1982 | Speck et al. |

(Continued)

FOREIGN PATENT DOCUMENTS

| | | |
|---|---|---|
| WO | WO 87/05491 | 9/1987 |
| WO | WO 87/05492 | 9/1987 |
| WO | WO 92/04924 | 4/1992 |
| WO | WO 97/04657 | 2/1997 |
| WO | 99/18894 | 4/1999 |

OTHER PUBLICATIONS

Bostrom et al., "Future directions: Augmentation of osteoporotic vertebral bodies," *Spine*, 22(24S):38S-42S (1997).

(Continued)

*Primary Examiner*—Corrine McDermott
*Assistant Examiner*—Cheryl Miller
(74) *Attorney, Agent, or Firm*—Matthew Scheele; Brian E. Szymczak

(57) ABSTRACT

An enhanced visibility composition for implantation from a remote source, so that the composition can be readily observed under fluoroscopy or other imaging techniques is disclosed. The compositions include a biocompatible matrix, such as a hard tissue implant material for example, and radiopaque particles mixed in the matrix. The radiopaque particles have a particle size between about 120μ and 2200μ, more preferably bout 350μ and 2200μ, even more preferably between about 450μ and 1600μ, and most preferably between about 570μ and 1150μ. Preferably the hard tissue implant and the radiopaque particles are formed or prepared in a slurry. Optionally, the enhanced visibility composition may further include additional radiopaque particles or contrast particles mixed in with the composition, which have a particle size between about 120μ and 350μ, preferably between about 120μ and 250μ.

21 Claims, 2 Drawing Sheets

U.S. PATENT DOCUMENTS

| | | | |
|---|---|---|---|
| 4,373,217 A | 2/1983 | Draenert | |
| 4,404,327 A | 9/1983 | Crugnola et al. | |
| 4,500,658 A * | 2/1985 | Fox | 523/117 |
| 4,554,686 A | 11/1985 | Baker | |
| 4,610,692 A | 9/1986 | Eitenmuller et al. | |
| 4,637,931 A | 1/1987 | Schmitz | |
| 4,728,570 A | 3/1988 | Ashman et al. | |
| 4,791,150 A | 12/1988 | Braden et al. | |
| 4,837,279 A | 6/1989 | Arroyo | |
| 4,900,546 A | 2/1990 | Posey-Dowty et al. | |
| 4,966,601 A | 10/1990 | Draenert | |
| 4,969,888 A | 11/1990 | Scholten et al. | |
| 5,015,101 A | 5/1991 | Draenert | |
| 5,112,354 A | 5/1992 | Sires | |
| 5,114,240 A * | 5/1992 | Kindt-Larsen et al. | 366/129 |
| 5,258,028 A * | 11/1993 | Ersek et al. | 623/11 |
| 5,282,861 A | 2/1994 | Kaplan | |
| 5,304,586 A | 4/1994 | Hammesfahr et al. | |
| 5,336,263 A | 8/1994 | Ersek et al. | |
| 5,336,699 A | 8/1994 | Cooke et al. | |
| 5,367,002 A | 11/1994 | Huang et al. | |
| 5,451,406 A * | 9/1995 | Lawin et al. | 424/423 |
| 5,476,880 A | 12/1995 | Cooke et al. | |
| 5,507,813 A * | 4/1996 | Dowd et al. | 623/23.63 |
| 5,512,610 A * | 4/1996 | Lin | 523/116 |
| 5,571,182 A | 11/1996 | Ersek et al. | |
| 5,574,075 A | 11/1996 | Draenert | |
| 5,676,146 A | 10/1997 | Scarborough | |
| 5,681,872 A | 10/1997 | Erbe | |
| 5,717,006 A * | 2/1998 | Daculsi et al. | 523/115 |
| 5,792,478 A | 8/1998 | Lawin et al. | |
| 5,795,922 A | 8/1998 | Demian et al. | |
| 5,837,752 A * | 11/1998 | Shastri et al. | 523/116 |
| 5,919,434 A * | 7/1999 | Dugstad et al. | 424/9.52 |
| 6,077,916 A * | 6/2000 | Laurencin et al. | 525/419 |
| 6,080,801 A * | 6/2000 | Draenert et al. | 523/115 |
| 6,103,254 A * | 8/2000 | Wallace et al. | 424/422 |

OTHER PUBLICATIONS

Convery et al., "The relative safety of polymethylmethacrylate" *J. of Bone and Joint Surg*, 57-A(1):57-64 (975).

Cotton et al., "Preoperative percutaneous injection of methyl methacrylate and N-butyl cyanoacrylate in vertebral hemangiomas" *Am J. Neuroradiol*, 17:137-142 (1996).

Cybulski, "Methods of surgical stabilization for metastatic disease of the spine" *Neurosurgery* 25(2):240-252 (1989).

Demian et al., "Regulatory perspective on characterization and testing of orthopedic bone cements" *Biomaterials* 19:1607-1618 (1998).

Deramond et al., "Percutaneous vertebroplasty with methylmethacrylate: technique, method, results" *Radiology*, 117(Supp):352 (1990).

Dierks et al., "Treatment of an infected mandibular graft using tobramycin-inpregnanted methymethacrylate beads: Report of a case" *J. Oral Maxillofac Surg*, 50:1243-1245 (1992).

Galibert et al., "Note preliminaire sur le traitement des angiomes vertebraux par vertebroplastie acrylique percutanee" *Neurochirugie*, 33:1266-168 (1987) (Partial summary translation included).

Gangi et al., "Percutaneous vertebroplasty guided by a combination of CT and fluoroscopy" *AJNR American Society of Neuroradiology*, 15:83-86 (Jan. 1994).

Goode et al., "Tobramycin-inpregnanted methylmethacrylate for mandible reconstruction" *Arch Otolaryngol Head Neck Surg* 118:201-204 (1992).

Harrington, "Anterior decompression and stabilization of the spine as a treatment for vertebral collapse and spinal cord compression from metastatic malignancy" *Clincal Orthopaedics and Related Research* 233:177-197 (1988).

Howmedia, Inc. (Brochure of) "Surgical Simplex® P-Radiopaque Bone Cement" *Howmedia, Inc.*, Pfizer hospital products group, Rutherford, New Jersey, 6 pages (Feb. 1995).

Jensen et al., "Percutaneous polymethylmethacrylate vertebroplasty in the treatment of osteoporotic vertebral body compression fractures: technical aspects" *AJNR American Society of Neuroradiology*, 18:1897-1904 (Nov. 1997).

Karmmerlen et al., "Vertebroplastic percutanee dans le traitement des metastases" *J. Radiol.* 70(10):557-562 (1989) (Partial summary translation included).

McLaughlin et al., "Blood clearance and acute pulmonary toxicity of methylmethacrylate in dogs after stimulated arthroplasty and intravenous injection" *J. of Bone and Joint Surg.*, 55-A(8):1621-1628 (1973).

Nicola et al., "Vertebral hemangioma: Retrograde embolization—Stabilization with methyl methacrylate" *Surg. Neurol.* 27:481-486 (1987).

O'Donnell et al., "Recurrence of giant-cell tumors of the long bones after curettage and packing with cement" *J. of Bone and Joint Surg.*, 76-A(12):1827-1833 (1994).

Persson et al., "Favourable results of acrylic cementation for giant cell tumors" *Acta Orthop Scand*, 55:209-214 (1984).

Phillips et al., "Cardiovascular effects of implanted acrylic bone cement" *British Medical Journal*, 3:460-461 (1971).

Shapiro, "Cranioplasty, vertebral body replacement, and spinal fusion with tobramycin-impregnated methylmethacrylate" *Neurosurgery*, 28(6):789-791 (1991).

Sundaresan et al., "Treatment of neoplastic epidural cord compression by vertebral body resection and stabilization" *J. Neurosurg*, 63:676-684 (1985).

Wang et al., "Safety of anterior cement fixation in the cervival spine: In vivo study of dog spine" *So. Medical J.*, 77(2):178-179 (1984).

Weill et al., "Spinal metastases: Indications for and results of percutaneous injection of acrylic surgical cement" *Radiology* 199(1):241-247 (1996).

Zimmer, Inc. (Brochure of) "Zimmer® Bone Cement—Cough-Type; Zimmer® L.V.C.® Bone Cement—Low Viscosity Radiopaque" Zimmer, Warsaw, Indianna pp. 1-7 (Feb. 1994).

PCT International Search Report for PCT/US98/21576, 2 pgs, mailed Feb. 26, 1999.

PCT International Preliminary Examination Report for PCT/US98/21576, 5 pgs, mailed Aug. 7, 2001.

PCT International Preliminary Examination Report for PCT/US98/21576, 5 pgs, mailed Jun. 22, 2000.

PCT Written Opinion for PCT/US98/21576, 5 pgs, mailed Nov. 17, 1999.

PCT Written Opinion for PCT/US98/21576, 6 pgs, mailed Oct. 22, 1999.

* cited by examiner

ENHANCED VISIBILITY MATERIALS FOR IMPLANTATION IN HARD TISSUE

This is a Continuation Application of U.S. Ser. No. 09/420,093 filed Oct. 18, 1999, issued as U.S. Pat. No. 6,231,615, titled "Enhanced Visibility Material For Implantation in Hard Tissue," which is a Divisional Application of U.S. Ser. No. 08/950,256 filed Oct. 14, 1997, issued as U.S. Pat. No. 6,309,420 with the same title.

TECHNICAL FIELD

The present invention relates to compositions for use as tissue implants, preferably hard tissue implants. More particularly, the present invention is directed to compositions which are more easily viewed by imaging techniques, during the implantation thereof, than compositions that are presently known and used. A particularly advantageous use of the present invention is for percutaneous injection of hard tissue implant materials, although the invention is not to be so limited.

BACKGROUND ART

Polymethylmethacrylate (PMMA) has been used in anterior and posterior stabilization of the spine for metastatic disease, as described by Sundaresan et al., "Treatment of neoplastic epidural cord compression by vertebral body resection and stabilization." *J Neurosurg* 1985; 63:676-684; Harrington, "Anterior decompression and stabilization of the spine as a treatment for vertebral collapse and spinal cord compression from metastatic malignancy." *Clinical Orthodpaedics and Related Research* 1988; 233:177-197; and Cybulski, "Methods of surgical stabilization for metastatic disease of the spine." *Neurosurgery* 1989; 25:240-252.

Deramond et al., "Percutaneous vertebroplasty with methyl-methacrylate: technique, method, results [abstract]." *Radiology* 1990; 117 (suppl):352; among others, have described the percutaneous injection of PMMA into vertebral compression fractures by the transpedicular or paravertebral approach under CT and/or fluoroscopic guidance. Percutaneous vertebroplasty is desirable from the standpoint that it is minimally invasive, compared to the alternative of surgically exposing the hard tissue site to be supplemented with PMMA or other filler.

The general procedure for performing percutaneous vertebroplasty includes the percutaneous injection of PMMA or other bone implant material into the damaged or fractured bone tissue of a vertebra. During injection of the bone implant material, fluoroscopic imaging or another imaging technique is used to track the path that the bone implant material takes as well as its final position upon implantation. Contrast agents such as barium sulfate powder are often used to aid the visibility of the bone implant material by imaging. However, the barium sulfate powders and other contrast agents presently used are generally very fine. This type of contrast agent is fairly effective once a given mass of the mixture of it with the bone implant material has accumulated at an implant site. However, for purposes of tracking the flow and leading edge surfaces of a bone implant material during injection, or for viewing small volumes of the implant material, the contrast agents presently used are inadequate.

This inadequacy becomes especially important during injection of liquid or flowable bone implant materials, as is the case with percutaneous vertebroplasty, since viewing of the path taken by the implant material is very important. That is because the bone implant material may take a path where it begins to enter the venous system, where it is not only unwanted, but where it could have very damaging effects. Thus, an improvement in the visibility of bone implant materials during injection is needed.

The use of radiographic contrast agents in a three dimensional, solid conglomerate of polymer particles which is used as a starting material for the preparation of bone cement is disclosed by Draenert in U.S. Pat. No. 5,574,075. The agents may be particulate, having a size range of between 5 and 300 μm. Draenert makes the three-dimensional conglomerate of polymeric particles, with the idea of converting the powder phase of the precursors of a PMMA bone cement mixture into a solid phase, similar to cube sugar.

Cooke et al., in U.S. Pat. No. 5,476,880, discloses the incorporation of sized, radiopaque particles into a PMMA bone composition that is additionally reinforced with previously sized reinforcing fibers. The preferred radiopaque agent is zirconium dioxide, which may be present at a level between 1-15% by weight of the powder. Barium sulfate may also be used. The radiopaque powder preferably has a diameter of about 1μ.

Accordingly, there exists a need for a more visible composition to enable the tracking of the path of implantation taken by an implantable bone composition, particularly flowable or liquid compositions which are implanted from a remote site, by injection or other means.

DISCLOSURE OF THE INVENTION

An enhanced visibility composition for implantation into hard tissue is disclosed as including a hard tissue implant material and radiopaque particles mixed in the hard tissue implant material. The radiopaque particles have a particle size between about 120μ and 2200μ, more preferably between about 350μ and 2000μ, even more preferably between about 450μ and 1600μ, and most preferably between about 570μ and 1150μ. Other acceptable particle size ranges are disclosed to include between about 350μ and 2200μ, between about 450μ and 2200μ, between about 570μ and 2200μ, between about 350μ and 1600μ, between about 350μ and 1150μ, and between about 450μ and 1150μ.

Preferably the hard tissue implant and the radiopaque particles, according to the present invention, are formed or prepared in a slurry for implantation. The hard tissue implant material preferably includes polymethyl methacrylate. Alternative hard tissue implant materials that may be mixed with the radiopaque particles include hydroxyapatite, various formulations of biocompatible calcium phosphates, biocompatible calcium sulfates, demineralized and/or mineralized bone particles, polymer based implants including polyglycolic acid and or polylactic acid compounds, collagen and/or collagen derivative preparations alone or in combination with other biomaterials, chitin and/or chitosan preparations, bioglasses including oxides of silicon, sodium, calcium and phosphorous and combinations thereof, and other known materials which are acceptable for use as hard tissue implant materials including osteogenic and osteoinductive compositions, and combinations thereof.

The radiopaque particles may include barium sulfate, tungsten, tantalum, zirconium, platinum, gold, silver, stainless steel, titanium, alloys thereof, combinations thereof, or other equivalent materials for use as radiographic agents in hard tissue implant materials that can be formed as particles.

Optionally, the enhanced visibility composition according to the present invention may further include additional radiopaque particles or contrast particles mixed in with the composition. The additional radiographic or contrast particles may have a particle size between about 120μ and 350μ, preferably between about 120μ and 250μ.

The additional radiopaque or contrast particles may include barium sulfate, bismuth subcarbonate, bismuth sulfate, powdered tungsten, powdered tantalum, zirconium, combinations thereof, or other equivalent materials for use as radiographic agents in hard tissue implant materials that can be formed as particles. Additionally, liquid or soluble contrast agents may be used, e.g., Metrizamide, disclosed in U.S. Pat. No. 3,701,771 or Iopromide, disclosed in U.S. Pat. No. 4,364,921. Both U.S. Pat. Nos. 3,701,771 and 4,364,921 are hereby incorporated by reference herein in their entireties. The composition of the additional radiopaque or contrast particles may, but need not be the same as the composition of the radiographic particles.

Further disclosed is a composition for percutaneous vertebroplasty comprising a slurry of biocompatible implant material and radiopaque markers having a particle size of between about 120μ and 2200μ. All of the size ranges given above for the radiographic particles are suitable for the radiopaque markers. Preferably, the radiopaque markers have a particle size between about 570μ and 1150μ. The biocompatible implant material of the slurry preferably includes polymethyl methacrylate. Alternative implant materials include hydroxyapatites, calcium phosphates, demineralized bone particles, and other known bone implant materials, including osteogenic and osteoinductive compositions.

The composition for percutaneous vertebroplasty may optionally include contrast particles having a particle size between about 120μ and 350μ.

Additionally, an injectable composition is described, which includes a biocompatible matrix which may include soft tissue implants as well as hard tissue implants, and radiopaque particles mixed within the biocompatible matrix. The radiopaque particles have a particle size between about 350μ and 2200μ, more preferably between about 450μ and 1600μ, and most preferably between about 570μ and 1150μ.

The biocompatible matrix and radiopaque particles preferably form a slurry. Preferably, the slurry comprises an injectable composition for implantation in hard tissue. Further, contrast particles having a particle size between about 120μ and 350μ may be included in the injectable composition.

BEST MODE FOR CARRYING OUT THE INVENTION

The percutaneous injection of polymethylmethacrylate (PMMA) is a recent technique of treating pain associated with acute vertebral body compression fractures that is showing a great deal of promise as an effective treatment method. The PMMA is in a slurry state when it is percutaneously injected. The slurry is prepared just prior to the injection by mixing a powder component, e.g., methyl methacrylate polymer, with a liquid component, e.g., methylmethacrylate monomer. Additional components such as copolymers (e.g., styrene,), accelerators (e.g., N,N-dimethyl paratoluidene), initiators (e.g., benzoyl peroxide), stabilizers (e.g., hydroquinone) and/or antibiotics (e.g., Tobramycin) may be included in the slurry. Note that the above are only examples of the many additives that are currently used in PMMA compositions for implantation, and the other known additives are acceptable for the purposes of the present invention.

Contrast agents such as barium sulfate and zirconium dioxide have also been added to the PMMA mixture. Contrast agents are typically in the form of fine powders having a very fine particle size on the order of a few microns. Upon injection of the PMMA into the vertebral body using, for example, a long 11 gauge cannula 5, the opacification of the PMMA increases, as viewed by an imaging technique such as fluoroscopy, or X-ray, CT, MRI or other accepted modality of medical imaging, as the volume of the PMMA accumulates at the implantation site.

Figure 1:
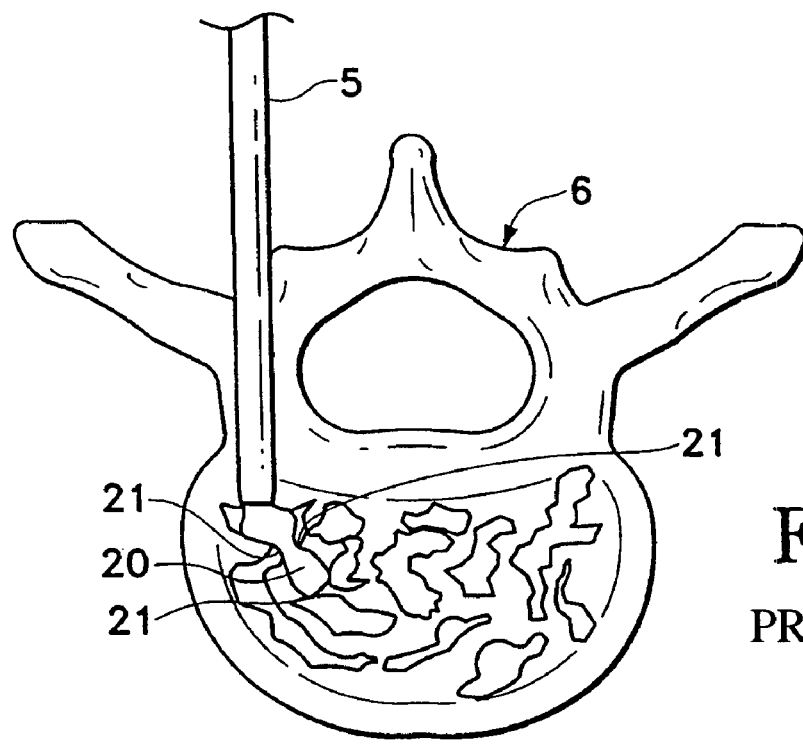
FIG. 1 is a sectional view of an injection of a prior art bone implant material into a damaged vertebra.

As indicated in FIG. 1, however, small volumes of the injected PMMA 20, when viewed under fluoroscopy, or other imaging technique, are difficult to discern. More specifically, it is often difficult to visually distinguish between the PMMA 20 and the bony landmarks 21 in the visual field, especially when the PMMA 20 has just begun to flow and the volume delivered is thus very low. In small volumes, the PMMA 20 appears as a very faint grayish hue when viewed under fluoroscopy. The gray hue becomes darker as more PMMA 20 is injected and the volume begins to accumulate at the implant site. However, better visualization of the implant material is required to track the flow of the implant material so as to prevent an inadvertent injection into a vein, which could transport the material to the lungs of the patient, occlude the vein. or cause other various forms of damage to the patient.

Figure 2:
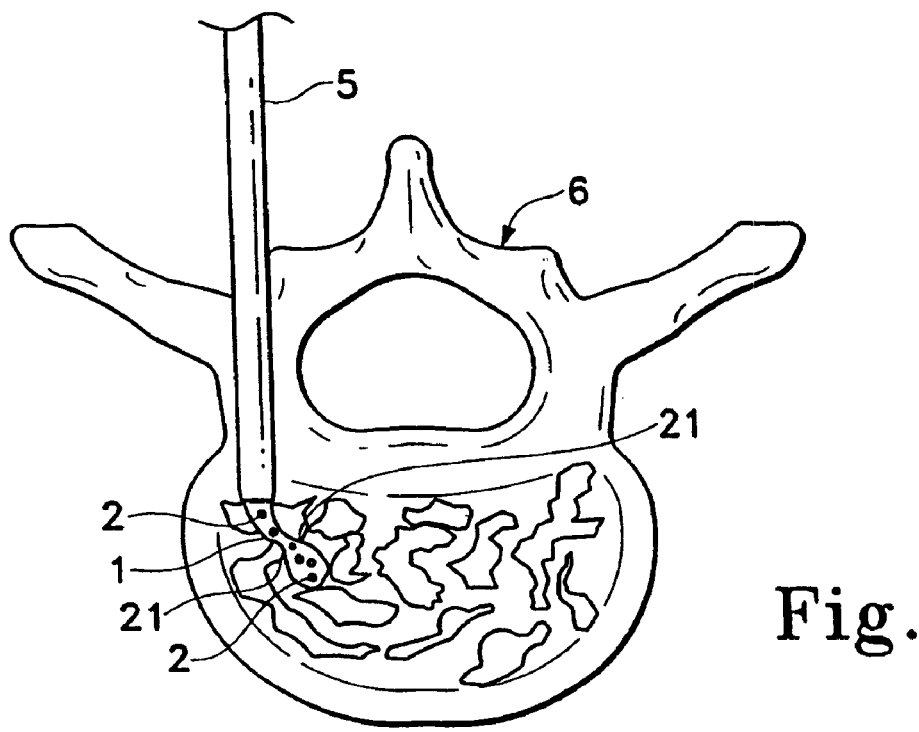
FIG. 2 is a sectional view of an injection of a bone implant material according to the present invention, into a damaged vertebra.

FIG. 2 indicates the enhanced visibility of an implant material 1 which is percutaneously injected into a vertebra 6, using an 11 gauge cannula 5, for example. In the example shown in FIG. 2, the composition 1 is exactly the same as the composition 20 shown in FIG. 2, except for an addition of larger particle radiopaque tracers 2. The radiopaque tracers are particles having a particle size between about 120μ and 2200μ. The particle size range of the tracers used may vary and include ranges such as: between about 350μ and 2200μ; between about 350μ and 2000μ; between about 570μ and 2200μ; between about 350μ and 1600μ; between about 350μ and 1150μ; between about 450μ and 1150μ; and between about 450μ and 1600μ. A preferred particle size range for the tracers is between about 570μ and 1150μ.

As illustrated in FIG. 2, the radiopaque tracers can be clearly and individually identified under fluoroscopy having a magnification of 4×, r other imaging technique as described above, as they exit the cannula 5, even during the initial flow of the implant material 1 from the cannula 5. Thus, an accumulation of the implant material is not required before accurate visual tracking can begin. Importantly, the flow of the material of the present invention can be easily viewed. Also the shape of the tracers 2 is readily identifiably and distinguishable from the bony landmarks 21 of the implant site.

The addition of radiopaque tracers 2 to the composition 1, increases the visibility of the composition without substantially effecting the viscosity of the composition. The addition of the tracers 2 creates a quasi-homogenous slurry in which the tracers appear as dark gray spots under fluoroscopy. The tracer particles are individually viewable under medical fluoroscopy at a magnification of 4× or greater.

The radiopaque tracers 2 may be added to the composition with or without a conventional contrast agent. Alternatively, the addition of significantly more particles having a particle size of about 120μ to 350μ, more preferably about 120μ to 250μ to the composition 20, in addition to a significantly lesser concentration of particles having a large size range of about 350μ to 2200μ, more preferably about 450μ and 1600μ, and most preferably between about 570μ and 1150μ. The larger concentration of small particles acts to enhance viewing of the accumulated mass of the implant, while the larger particles perform the "tracing" function, allowing the flow of the implant to be viewed under fluoroscopy or other medical imaging device.

The addition of tracer particles to an implantable composition enhances the visibility of the composition, particularly enabling the viewing of the flow, without significantly increasing the viscosity or setting times of the composition. Alternatively, if one were to merely increase the concentration of the convention fine powder contrast agent, to attempt to enhance the visibility of the composition, significantly increases in the viscosity of the composition ensue, and the polymerization times may be adversely effected. Of course, an increase in viscosity adversely effects the ability to effectively inject a composition. Not only does it become more difficult to pass the composition through whatever injection apparatus is to be used, but the composition also is less able to permeate all of the posrosities, defects, or other tortuous pathways which are intended to be filled by the implantable composition, since it is simply less flowable and less dispersible.

Thus, the simple addition of more fine powder radiopaque contrast agent is not an acceptable solution to making a more visible implantable composition. This makes the slurry too viscous for adequate perfusion throughout the vertebral body or other hard tissue site and additionally requires larger injection forces, thereby increasing the risk of accidents, such as breaking the delivery cannula during injection.

However, the addition of tracer particles having size ranges as indicated above, in small concentrations, enhances the visualization of the composition, as illustrated in FIG. 2, without increasing the viscosity or the pressure requirements to inject the composition. Nor are the polymerization times of the resultant composition substantially shortened or otherwise adversely effected.

Figure 3:
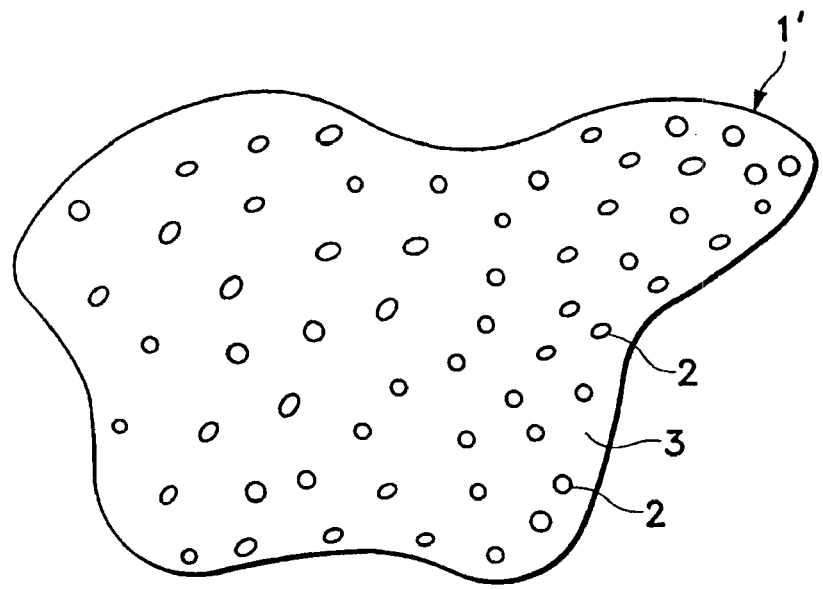
FIG. 3 is a schematic representation of a hard tissue implant matrix, with radiopaque markers mixed therein according to the present invention.

As illustrated in FIG. 3, the radiopaque tracers 2 according to the present invention can also be effectively used in a composition 1' without the use of a contrast agent. A viscosity adjustment of the composition, in the case of PMMA can be made by simply increasing the powder phase of the polymer to make up for any decrease in viscosity that might occur by leaving out the contrast agent.

Figure 4:
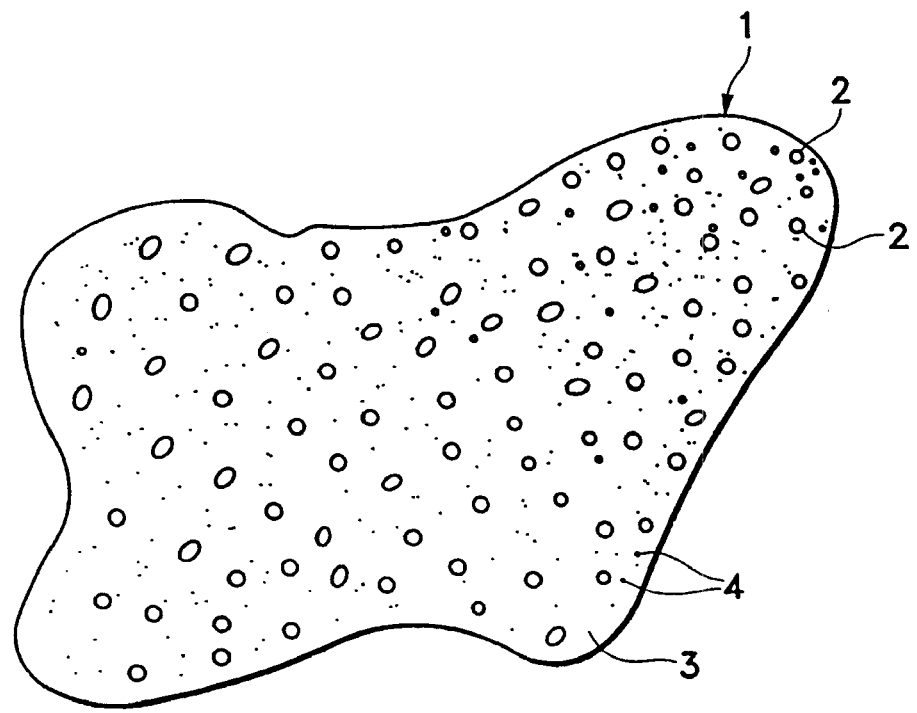
FIG. 4 is a schematic representation of a hard tissue implant matrix, with radiopaque markers and a small particle contrast agent mixed therein according to the present invention.

The radiopaque particles may be formed from barium sulfate, zirconium dioxide, tantalum, tungsten, platinum, gold, silver, stainless steel, titanium, alloys thereof, combinations thereof, or other known materials used as contrast agents for implants. Additionally, combinations of the particles may be added to the mixture. When a contrast agent is also included in the mixture, the contrast agent may be made from the same materials as the tracers, or from a different material or mixture of material particles. The same materials disclosed above as being acceptable for use as tracer particles are acceptable for use as contrast agents. Similarly, when two ranges of tracer particle sizes are used, as illustrated in FIG. 4, the smaller size group 4 may be made from the same materials as the larger size group 2, or from a different material or mixture of material particles. If used, the smaller size particles should be formed from particles having a particle size between about 120μ and 350μ, preferably between about 120μ and 250μ

The matrix 3 or implant material into which the radiopaque markers 2 may be mixed, is not limited to PMMA, but may also be added to hydroxyapatite mixtures, calcium phosphate mixtures, calcium sulfate mixtures, demineralized or mineralized bone particle compositions, polymer based implants including polyglycolic acid and or polylactic acid compounds, collagen and/or collagen derivative preparations alone or in combination with other biomaterials, chitin and/or chitosan preparations, bioglasses including oxides of silicon, sodium, calcium and phosphorous and combinations thereof, and other known materials which are acceptable for use as hard tissue implant materials including osteogenic and osteoinductive compositions, and combinations thereof, as well as other known hard tissue fillers and implant materials. Additionally, the tracers may be included in a matrix for soft tissue implantation, including materials such as silicon, collagens, gelatins, and various other soft tissue implant materials.

Although the present invention is preferably directed at remotely deliverable hard tissue implant materials, and particularly slurries, it is not to be so limited, but may be used in other compositions where an enhanced visualization of the material is desired. For example, the tracers could be used in a more viscous composition of PMMA to be implanted manually at the implantation site, e.g. the anchoring of an acetabular cup or knee prosthesis.

EXAMPLES

Example 1

A slurry of PMMA is prepared from about 10 g of a powder phase which is 15% w/w polymethylmethacrylate, 74% w/w methacrylate-styrene copolymer, 10% w/w commercially available barium sulfate powder (e.g., E-Z-EM, Westbury, N.Y.), and 1% w/w tracer particles made of barium sulfate particles having a particle size within the range of between about 570 and 1150μ. To the powder phase is added about 6-9 cc of a liquid phase made up of about 97.4% v/v methacrylate monomer; about 2.6% v/v N,N-dimethyl-p-toluidene; and 75∓15 ppm hydroquinone. The slurry is thoroughly mixed until a cake glaze like consistency is reached, at which time the composition is ready for implantation.

Example 2

A 10 cc volume slurry of PMMA is prepared from a powder phase which is 15% w/w polymethylmethacrylate, 75% w/w methacrylate-styrene copolymer, and 10% w/w tracer particles made of a mixture of barium sulfate particles and tungsten particles, each having a particle size within the range of between about 570 and 1150μ.

What is claimed is:

1. An injectable hard tissue implant composition comprising:
   a settably hardenable, flowable matrix comprising polymethylmethacrylate;
   radiopaque tracer particles in said flowable matrix, said radiopaque tracer particles comprising at least particles having a size between about 350μ and 2200μ and present in an amount so as to be individually visible during implantation; and
   radiopaque contrast particles comprising at least particles having a particle size between about 120μ and 350μ;
   wherein said contrast particles enhance the visibility of said matrix, and
   wherein said radiopaque tracer particles visibly indicate flow of said matrix during implantation.

2. The injectable composition of claim 1, wherein said radiopaque tracer particles comprise at least particles having a size between about 570µ and 2200µ.

3. The injectable composition of claim 1, wherein said radiopaque tracer particles comprise at least particles having a size between about 450µ and 1600µ.

4. The injectable composition of claim 1, wherein said radiopaque tracer particles comprise at least particles having a size between about 570µ and 1150µ.

5. The injectable composition of claim 1, wherein said radiopaque contrast particles comprise at least particles having a size between about 120µ and 250µ.

6. The injectable composition of claim 1, wherein the radiopaque tracer particles is selected from the group consisting of barium sulfate, tungsten, tantalum, zirconium, platinum, gold, silver, stainless steel, titanium, alloys thereof, combinations thereof, and equivalent materials used as radiographic agents in hard tissue implant materials that can be formed as particles.

7. The injectable composition of claim 1, wherein the radiopaque contrast particles is selected from the group consisting of barium sulfate, bismuth subcarbonate, bismuth sulfate, powdered tungsten, powdered tantalum, zirconium, combinations thereof, and equivalent materials for use as radiographic agents in hard tissue implant materials that can be formed as particles.

8. The injectable composition of claim 1, wherein the matrix and radiopaque tracer particles comprise a slurry.

9. The injectable composition of claim 8, wherein the slurry comprises an injectable composition for hard tissue implantation.

10. The injectable composition of claim 1, wherein the radiopaque tracer particles comprises about 1% of the total weight of the composition.

11. An injectable hard tissue implant composition comprising:
   a settably hardenable, flowable matrix comprising at least polymethylmethacrylate;
   radiopaque tracer particles,
   wherein the size of the radiopaque tracer particles comprises at least particles having a size between about 350µ and 2200µ and wherein the amount of radiopaque tracer particles present is such that radiopaque tracer particles are individually visible under fluoroscopy during implantation to visually indicate flow of the injectable composition during implantation; and
   radiopaque contrast particles consisting of particles having a particle size between about 120µ and 350µ wherein the contrast particles enhance the visibility of said matrix.

12. The injectable composition of claim 11, wherein the radiopaque tracer particles is selected from the group consisting of barium sulfate, tungsten, tantalum, zirconium, platinum, gold, silver, stainless steel, titanium, alloys thereof combinations thereof, and equivalent materials used as radiographic agents in hard tissue implant materials that can be formed as particles.

13. The injectable composition of claim 11, wherein the radiopaque contrast particles is selected from the group consisting of barium sulfate, bismuth subcarbonate, bismuth sulfate, powdered tungsten, powdered tantalum, zirconium, combinations thereof, and equivalent materials for use as radiographic agents in hard tissue implant materials that can be formed as particles.

14. The injectable composition of claim 11, wherein the amount of radiopaque tracer particles comprises about 1% of the total weight of the composition.

15. The injectable composition of claim 11, wherein the radiopaque tracer particles comprise at least particles sized between about 570µ and 2200µ.

16. The injectable composition of claim 11, wherein the radiopaque tracer particles comprise at least particles sized between about 450µ and 1600µ.

17. The injectable composition of claim 11, wherein the radiopaque tracer particles comprise at least particles sized between about 570µ and 1150µ.

18. The injectable composition of claim 11, wherein the amount of radiopaque tracer particles comprises about 10% of the total weight of the composition.

19. The injectable composition of claim 11 wherein the radiopaque tracer particles comprise barium sulfate.

20. An enhanced visibility composition for implantation into tissue comprising:
   a hard tissue implant material including a settably hardenable, flowable matrix comprising polymethylmethacrylate;
   radiopaque tracer particles in said flowable matrix, said radiopaque tracer particles comprising at least particles having a size between about 350µ and 2200µ and present in an amount so as to be individually visible during implantation; and
   radiopaque contrast particles comprising at least particles having a particle size between about 120µ and 350µ;
   wherein said contrast particles enhance the visibility of said matrix; and
   wherein said radiopaque tracer particles visibly indicate flow of said matrix during implantation.

21. An injectable hard tissue implant composition comprising:
   a settably hardenable, flowable matrix comprising polymethylmethacrylate;
   radiopaque tracer particles in said flowable matrix, said radiopaque tracer particles comprising at least particles having a size between about 350µ and 2200µ and present in an amount so as to be individually visible during implantation; and
   radiopaque contrast particles comprising at least particles having a particle size between about 120µ and 350µ;
   wherein said contrast particles enhance the visibility of said matrix, and wherein said radiopaque tracer particles visibly indicate flow of said matrix during implantation, and wherein the radiopaque tracer particles comprise about 1% of the total weight of the composition, and wherein the radiopaque tracer particles comprises a mixture of barium sulphate and tungsten particles.

* * * * *